(12) United States Patent
Heckel

(10) Patent No.: US 9,037,447 B2
(45) Date of Patent: May 19, 2015

(54) SYSTEMS AND METHODS FOR PHASE PREDICTIVE IMPEDANCE LOSS MODEL CALIBRATION AND COMPENSATION

(75) Inventor: Donald W. Heckel, Thornton, CO (US)

(73) Assignee: Covidien LP, Mansfield, MA (US)

( * ) Notice: Subject to any disclaimer, the term of this patent is extended or adjusted under 35 U.S.C. 154(b) by 560 days.

(21) Appl. No.: 13/360,289

(22) Filed: Jan. 27, 2012

(65) Prior Publication Data

US 2013/0197874 A1    Aug. 1, 2013

(51) Int. Cl.

| | |
|---|---|
| *G06F 17/50* | (2006.01) |
| *A61B 18/12* | (2006.01) |
| *A61B 18/14* | (2006.01) |
| *A61B 17/00* | (2006.01) |
| *A61B 18/00* | (2006.01) |

(52) U.S. Cl.
CPC ......... *A61B 18/1206* (2013.01); *A61B 18/1402* (2013.01); *A61B 18/1445* (2013.01); *A61B 2017/00725* (2013.01); *A61B 2018/00178* (2013.01); *A61B 2018/0075* (2013.01); *A61B 2018/00755* (2013.01)

(58) Field of Classification Search
None
See application file for complete search history.

(56) References Cited

U.S. PATENT DOCUMENTS

| | | | |
|---|---|---|---|
| 5,099,840 A | | 3/1992 | Goble et al. |
| 5,502,392 A | * | 3/1996 | Arjavalingam et al. ...... 324/638 |
| 5,743,900 A | | 4/1998 | Hara |
| 5,843,021 A | | 12/1998 | Edwards et al. |
| 6,019,757 A | | 2/2000 | Scheldrup |
| 6,171,304 B1 | | 1/2001 | Netherly |
| 6,322,558 B1 | | 11/2001 | Taylor et al. |
| 6,701,335 B2 | * | 3/2004 | Pupalaikis .................... 708/300 |
| 6,870,359 B1 | * | 3/2005 | Sekel .................... 324/750.02 |
| D574,323 S | | 8/2008 | Waaler |
| 7,755,371 B2 | * | 7/2010 | Wells ............................ 324/713 |
| 2002/0005668 A1 | * | 1/2002 | Couture ........................... 307/98 |

(Continued)

FOREIGN PATENT DOCUMENTS

| | | |
|---|---|---|
| CN | 101862219 A | 10/2010 |
| DE | 179607 | 3/1905 |

(Continued)

OTHER PUBLICATIONS

European Search Report issued in corresponding EP Application No. 13151437.4 dated May 21, 2013.

(Continued)

*Primary Examiner* — Saif Alhija
*Assistant Examiner* — Cuong Luu

(57) ABSTRACT

The systems and methods of the present disclosure calibrate impedance loss model parameters associated with an electrosurgical system having no external cabling or having external cabling with a fixed or known reactance, and obtain accurate electrical measurements of a tissue site by compensating for impedance losses associated with the transmission line of an electrosurgical device using the calibrated impedance loss model parameters. A computer system stores voltage and current sensor data for a range of different test loads and calculates sensed impedance values for each test load. The computer system then predicts a phase value for each load using each respective load impedance value. The computer system back calculates impedance loss model parameters including a source impedance parameter and a leakage impedance parameter based upon the voltage and current sensor data, the predicted phase values, and the impedance values of the test loads.

17 Claims, 13 Drawing Sheets

(56) References Cited

U.S. PATENT DOCUMENTS

| | | | |
|---|---|---|---|
| 2004/0114290 A1* | 6/2004 | Kehrli | 361/84 |
| 2005/0113819 A1 | 5/2005 | Wham | |
| 2006/0224152 A1* | 10/2006 | Behnke et al. | 606/34 |
| 2007/0173804 A1 | 7/2007 | Wham et al. | |
| 2008/0059092 A1* | 3/2008 | Pupalaikis et al. | 702/66 |
| 2008/0204054 A1* | 8/2008 | Wells | 324/713 |
| 2009/0018536 A1 | 1/2009 | Behnke | |
| 2009/0066438 A1* | 3/2009 | Kim et al. | 333/17.3 |
| 2009/0234353 A1 | 9/2009 | McPherson | |
| 2010/0121318 A1 | 5/2010 | Hancock et al. | |
| 2010/0121595 A1* | 5/2010 | Pupalaikis et al. | 702/67 |
| 2010/0179534 A1* | 7/2010 | Podhajsky et al. | 606/34 |
| 2010/0179535 A1* | 7/2010 | Podhajsky et al. | 606/34 |
| 2011/0098695 A1 | 4/2011 | Brannan | |
| 2011/0112526 A1 | 5/2011 | Fritz et al. | |
| 2011/0144635 A1 | 6/2011 | Harper et al. | |
| 2012/0013416 A1* | 1/2012 | Kim et al. | 333/17.3 |
| 2012/0239020 A1 | 9/2012 | Cunningham | |
| 2012/0239025 A1 | 9/2012 | Smith | |
| 2012/0239026 A1 | 9/2012 | Orszulak | |
| 2012/0253342 A1 | 10/2012 | Jensen | |
| 2012/0265194 A1 | 10/2012 | Podhajsky | |
| 2012/0265195 A1 | 10/2012 | Gilbert | |
| 2012/0283731 A1 | 11/2012 | Unger | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008058737 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1707144 A1 | 10/2006 |
| EP | 1776929 | 4/2007 |
| EP | 2301463 A1 | 3/2011 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 63 005876 | 1/1988 |
| JP | 2002-065690 | 3/2002 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO06/050888 | 5/2006 |
| WO | 2008063195 A1 | 5/2008 |
| WO | WO08/053532 | 5/2008 |
| WO | 2011126580 A2 | 10/2011 |

OTHER PUBLICATIONS

European Search Report issued in corresponding EP Application No. 13151439.0 dated Apr. 29, 2013.
U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/485,083, filed May 31, 2012, Robert J. Behnke, II.
U.S. Appl. No. 13/540,347, filed Jul. 2, 2012, Ronald J. Podhajsky.
U.S. Appl. No. 13/593,550, filed Aug. 24, 2012, Ronald J. Podhajsky.
U.S. Appl. No. 13/584,192, filed Aug. 13, 2012, Joseph D. Brannan.
U.S. Appl. No. 13/587,400, filed Aug. 16, 2012, James H. Orszulak
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'"Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

(56) References Cited

OTHER PUBLICATIONS

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Zlatanovic M., "Sensors in Diffusion Plasma Processing" Microelectronics 1995; Proceedings 1995; 20$^{th}$ International Conference CE on NIS, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed,"The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.

(56) References Cited

OTHER PUBLICATIONS

International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
Pre-Appeal Examination Report issued in counterpart Japanese Patent Application No. 2013-008869 dated Feb. 4, 2015.
European Search Report issued in corresponding EP Application No. 14192250.0 dated Feb. 19, 2015.

\* cited by examiner

SYSTEMS AND METHODS FOR PHASE PREDICTIVE IMPEDANCE LOSS MODEL CALIBRATION AND COMPENSATION

BACKGROUND

1. Technical Field

The present disclosure generally relates to electrosurgery. More particularly, the present disclosure relates to systems and methods for compensating for losses to obtain accurate electrical measurements in cordless or fixed-reactance cabled electrosurgical systems.

2. Background of Related Art

Electrosurgery involves the application of high-frequency electric current to cut or modify biological tissue during a surgical procedure. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The alternating current typically has a frequency above 100 kilohertz to avoid muscle and/or nerve stimulation.

During electrosurgery, the alternating current generated by the electrosurgical generator is conducted through tissue disposed between the active and return electrodes. The tissue's impedance converts the electrical energy (also referred to as electrosurgical energy) associated with the alternating current into heat, which causes the tissue temperature to rise. The electrosurgical generator controls the heating of the tissue, by controlling the electric power (i.e., electrical energy per time) provided to the tissue. Although many other variables affect the total heating of the tissue, increased current density usually leads to increased heating. The electrosurgical energy is typically used for cutting, dissecting, ablating, coagulating, and/or sealing tissue.

An electrosurgical generator includes a controller that controls the power applied to the tissue over some time period. The power applied to the tissue is controlled based upon power measurements and a power level set by the user or a power level needed to achieve a desired tissue effect. The power measurements are obtained by measuring the voltage and current of the RF signal generated by the RF output stage of the electrosurgical generator and calculating power based upon the measured voltage and current.

The voltage and current measured by the sensors of the electrosurgical generator, however, may not equal the actual voltage and current applied to the tissue because of RF impedance losses in the transmission line connecting the RF output stage of the electrosurgical generator to the electrodes of the electrosurgical instrument. As a result, the power calculations may be inaccurate and may lead to improper control of the electrosurgical energy applied to the tissue.

The affect of the RF impedance losses on the power and impedance calculations may be reduced by more accurately sampling the phase between the voltage and the current. However, this method requires greater computational complexity and more expensive high-speed hardware.

SUMMARY

The systems and methods of the present disclosure accurately determine the actual power applied to tissue and/or the actual impedance at the tissue site based on a predicted phase value. The disclosed methods for predicting the phase value are simple, require low computational complexity, and may be implemented using commonly available microprocessors, field programmable gate arrays (FPGAs), or digital signal processors (DSPs).

In one aspect, the present disclosure features a method of determining an impedance loss model parameter associated with a transmission line within an electrosurgical system. According to this method, a voltage and a current applied to a load coupled to an output of an electrosurgical system are sensed to obtain a sensed voltage and a sensed current, a sensed impedance value is calculated based upon the sensed voltage and the sensed current, a phase value is predicted based upon the sensed impedance value to obtain a predicted phase value, and the impedance loss model parameter is calculated based upon the predicted phase value, the sensed voltage, the sensed current, and a desired load impedance value.

The impedance loss model parameter may be a source impedance parameter and the source impedance parameter may be calculated by back calculating the source impedance parameter. The impedance loss model parameter may be a leakage impedance parameter and the leakage impedance parameter may be calculated by back calculating the leakage impedance parameter.

The impedance loss model parameter may be calculated by (1) converting the sensed voltage to a peak voltage value based upon the predicted phase value, (2) converting the sensed current to a peak current value based upon the predicted phase value, and (3) back calculating the impedance loss model parameter based upon the peak voltage value, the peak current value, and the desired load impedance value.

In another aspect, the present disclosure features a method of determining impedance loss model parameters associated with an electrosurgical device. According to this method, a voltage and a current applied to each of a plurality of loads separately coupled to an output of an electrosurgical device are sensed to obtain a plurality of sensed voltages and a plurality of sensed currents. Next, a plurality of sensed impedance values is calculated based upon the plurality of sensed voltages and the plurality of sensed currents. Next, a plurality of phase values is predicted based upon the plurality of sensed impedance values. Next, a source impedance parameter is calculated based upon a first predicted phase value of the plurality of phase values, a first sensed voltage of the plurality of sensed voltages, a first sensed current of the plurality of sensed currents, and a first predetermined load impedance value corresponding to a first load of the plurality of loads. Similarly, a leakage impedance parameter is calculated based upon a second predicted phase value of the plurality of phase values, a second sensed voltage of the plurality of sensed voltages, a second sensed current of the plurality of sensed currents, and a second predetermined load impedance value corresponding to a second load of the plurality of loads.

The plurality of phase values may be predicted based upon a polynomial function of the plurality of sensed impedance values. The polynomial function may be a third-order polynomial function. The plurality of loads may include loads rated between 0 ohms and 5000 ohms The source impedance parameter may be calculated by (1) converting the first sensed voltage to a first peak voltage value based upon the predicted first phase value; (2) converting the first sensed current to a first peak current value based upon the predicted first phase value; (3) calculating a first output voltage value based upon the first peak voltage value, the first peak current value, and a previous source impedance parameter; (4) calculating a first output current value based upon the first output voltage value, the peak current value, and a previous leakage impedance parameter; and (5) back calculating the source impedance parameter based upon the first output current value, the first predetermined load impedance value, the first peak voltage value, and the first peak current value.

The source impedance parameter may be back calculated by (1) back calculating a desired output voltage value by multiplying the first output current value by the first predetermined load impedance value, (2) back calculating a desired source voltage value by subtracting the desired output voltage value from the first peak voltage value, and (3) back calculating the source impedance parameter by dividing the desired source voltage value by the first peak current value. The first predetermined load impedance value may be less than the second predetermined load impedance value.

The method of determining impedance loss model parameters associated with an electrosurgical device may further include sensing an impedance of each load of the plurality of loads using an impedance meter to obtain a plurality of predetermined load impedance values. The plurality of predetermined load impedance values may include the first predetermined load impedance value and the second predetermined load impedance value.

The leakage impedance parameter may be calculated by (1) converting the second sensed voltage to a second peak voltage value based upon the predicted second phase value; (2) converting the second sensed current to a second peak current value based upon the predicted second phase value; (3) calculating a second output voltage value based upon the second peak voltage value, the second peak current value, and the previous source impedance parameter; and (4) back calculating the leakage impedance parameter based upon the second output voltage value, the second predetermined load impedance value, and the second peak current value. The previous source impedance parameter and the previous leakage impedance parameter may be set to initial values before a first iteration.

The leakage impedance parameter may be back calculated by (1) back calculating a desired output current value by dividing the second output voltage value by the second predetermined load impedance value, (2) back calculating a desired current value by subtracting the desired output current from the second peak current value, and (3) back calculating the leakage impedance parameter by dividing the desired current value by the second output voltage value.

The leakage impedance parameter may further be calculated by (1) iterating the steps of calculating a first output voltage value, (2) calculating a first output current value, (3) back calculating the source impedance parameter, (4) calculating a second output voltage value, and (5) back calculating the leakage impedance parameter.

In yet another aspect, the present disclosure features a computer system for calibrating measurement circuitry of an electrosurgical device. The computer system includes a memory, a processor coupled to the memory, and a communications interface. The memory stores data including a plurality of sensor voltage values, a plurality of sensor current values, a plurality of predicted phase values, and a plurality of predetermined load impedance values.

The processor calculates a source impedance parameter based upon a first predicted phase value of the plurality of phase values, a first sensed voltage of the plurality of sensed voltages, a first sensed current of the plurality of sensed currents, and a first predetermined load impedance value. The processor also calculates a leakage impedance parameter based upon a second predicted phase value of the plurality of phase values, a second sensed voltage of the plurality of sensed voltages, a second sensed current of the plurality of sensed currents, and a second predetermined load impedance value. The communications interface transmits the source impedance parameter and the leakage impedance parameter to the measurement circuitry of the electrosurgical device.

The communications interface may receive the plurality of sensor voltage values and the plurality of sensor current values from the electrosurgical device and may store the plurality of sensor voltage values and the plurality of sensor current values in the memory.

The processor may be a first processor, the source impedance parameter may be a first source impedance parameter, the leakage impedance parameter may be a first leakage impedance parameter, and the computer system may further include a second processor.

The second processor calculates a second source impedance parameter based upon the first predicted phase value of the plurality of phase values, the first sensed voltage of the plurality of sensed voltages, the first sensed current of the plurality of sensed currents, and the first predetermined load impedance value. The second processor also calculates a second leakage impedance parameter based upon the second predicted phase value of the plurality of phase values, the second sensed voltage of the plurality of sensed voltages, the second sensed current of the plurality of sensed currents, and the second predetermined load impedance value. The second processor then averages the first source impedance parameter and the second source impedance parameter to obtain an average source impedance parameter, and averages the first leakage impedance parameter and the second leakage impedance parameter to obtain an average leakage impedance parameter. The communications interface may transmit the average source impedance parameter and the average leakage impedance parameter to the measurement circuitry of the electrosurgical device.

BRIEF DESCRIPTION OF THE DRAWINGS

Various embodiments of the present disclosure are described with reference to the accompanying drawings wherein.

DETAILED DESCRIPTION

The systems and methods of the present disclosure calibrate an impedance loss model associated with the transmission lines within electrosurgical systems. These systems and methods involve sensing the voltage and current applied to a test load coupled to the output of the electrosurgical system, calculating a sensed impedance, predicting a phase between the voltage and current based upon the sensed impedance, and calculating at least one internal impedance value based upon the measured voltage and current, the predicted phase between the voltage and current, and a predetermined impedance of the test load.

The systems and methods of the present disclosure also compensate for impedance losses in the transmission lines of the electrosurgical systems using the calibrated impedance loss model. These systems and methods involve sensing a voltage and a current of an electrosurgical signal generated by and applied to a tissue site by the electro surgical system, predicting a phase value based upon the sensed voltage and the sensed current, calculating at least one metric at the tissue site based upon the sensed voltage, the sensed current, the predicted phase value, and at least one impedance loss model parameter associated with the transmission lines or cables of the electrosurgical systems.

Figure 1:
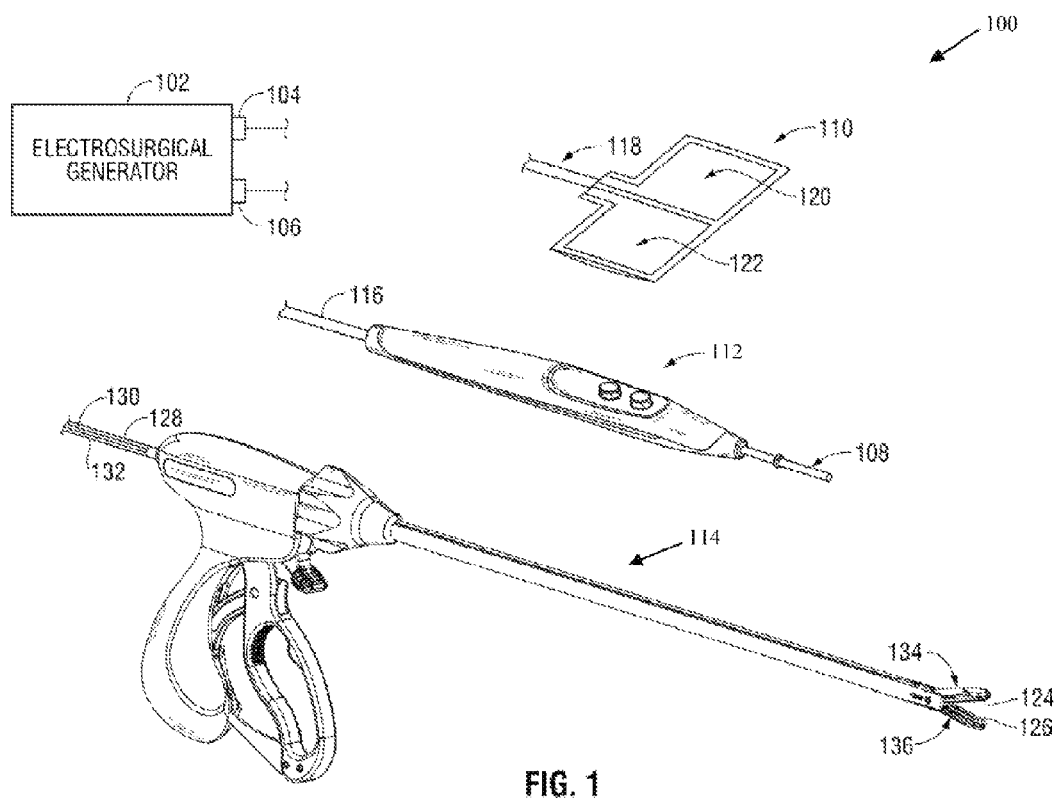
FIG. 1 is a perspective view of components of an electrosurgical system according to embodiments of the present disclosure.

FIG. 1 is a perspective view of an electrosurgical system 100 that incorporates the calibration and compensation systems and methods according to embodiments of the present disclosure. The electrosurgical system 100 includes an electrosurgical generator 102 for generating electrosurgical energy and various electrosurgical instruments 112, 114 that electrically connect to the generator 102 and deliver the electrosurgical energy to tissue during a surgical procedure. As described in further detail below, the generator 102 includes electronic circuitry (e.g., analog and digital circuitry) that measures the impedance and calculates the power delivered to tissue.

The electrosurgical generator 102 includes a plurality of outputs, e.g., terminals 104 and 106, for interfacing with various electrosurgical instruments, e.g., the return pad 110, the monopolar active electrode 112, and the bipolar electrosurgical forceps 114. The return pad 110 and the monopolar active electrode 112 are used to perform monopolar electrosurgical procedures and the bipolar electrosurgical forceps is used to perform bipolar electrosurgical procedures. The electrosurgical generator 102 includes electronic circuitry that generates radio frequency power for various electrosurgical modes (e.g., cutting, coagulating, or ablating) and procedures (e.g., monopolar, bipolar, or vessel sealing).

The electrosurgical instruments 112, 114 include one or more electrodes for treating tissue of a patient (e.g., an electrosurgical cutting probe or ablation electrodes (not shown)). Electrosurgical energy, e.g., radio frequency (RF) current, is supplied to the monopolar active electrode 112 by the electrosurgical generator 102 via a supply line 116, which is connected to an active terminal 104 of the electrosurgical generator 102, allowing the monopolar active electrode 112 to coagulate, seal, ablate and/or otherwise treat tissue. The electrosurgical current returns from the tissue to the generator 102 via a return line 118 of the return pad 110 to a return terminal 106 of the electrosurgical generator 102. The active terminal 104 and the return terminal 106 may include connectors (not shown) configured to interface with plugs (also not shown) disposed at the end of the supply line 116 of the monopolar active electrode 112 and at the end of the return line 118 of the return pad 110.

The return pad 110 includes return electrodes 120 and 122 that are arranged to minimize the risk of tissue damage by maximizing the overall contact area with the patient's tissue. In addition, the electrosurgical generator 102 and the return pad 110 may be configured to monitor tissue-to-patient contact to ensure that sufficient contact exists between the return pad 110 and the patient to minimize the risk of tissue damage.

The electrosurgical system 100 also includes a bipolar electrosurgical forceps 114 having electrodes 124, 126 for treating tissue of a patient. The bipolar electrosurgical forceps 114 includes opposing jaw members 134, 136. The first jaw member 134 includes an active electrode 124 and the second jaw member 136 includes a return electrode 126. The active electrode 124 and the return electrode 126 are connectable to the electrosurgical generator 102 through cable 128, which includes a supply line 130 and a return line 132. The supply line 130 is connectable to the active terminal 104 and the return line 132 is connectable to the return terminal 106. The bipolar electrosurgical forceps 114 connects to the active terminal 104 and the return terminal 106 of the electrosurgical generator 102 through a plug (not explicitly shown) disposed at the end of the cable 128.

The electrosurgical generator 102 may include a plurality of connectors to accommodate various types of electrosurgical instruments (e.g., monopolar active electrode 112 and bipolar electrosurgical forceps 114). The electrosurgical generator 102 may also include a switching mechanism (e.g., relays) to switch the supply of RF energy between the connectors. For example, when the monopolar active electrode 112 is connected to the electrosurgical generator 102, the switching mechanism switches the supply of RF energy to only the monopolar plug. The active terminal 104 and the return terminal 106 may be coupled to a plurality of connectors (e.g., inputs and outputs) of the electrosurgical generator 102 to power a variety of instruments.

The electrosurgical generator 102 includes suitable input controls (e.g., buttons, activators, switches, or touch screens) for controlling the electrosurgical generator 102. In addition, the electrosurgical generator 102 may include one or more display screens for providing the user with a variety of output information (e.g., intensity settings and treatment complete indicators). The controls allow the user to adjust parameters of the RF electrical energy (e.g., the power or the waveform) so that they are suitable for a particular task (e.g., coagulating, tissue sealing, or cutting). The electrosurgical instruments 112 and 114 may also include a plurality of input controls that may be redundant with certain input controls of the electrosurgical generator 102. Placing the input controls at the electrosurgical instruments 112 and 114 allows for easier and faster modification of RF energy parameters during the surgical procedure without requiring interaction with the electrosurgical generator 102.

Figure 2:
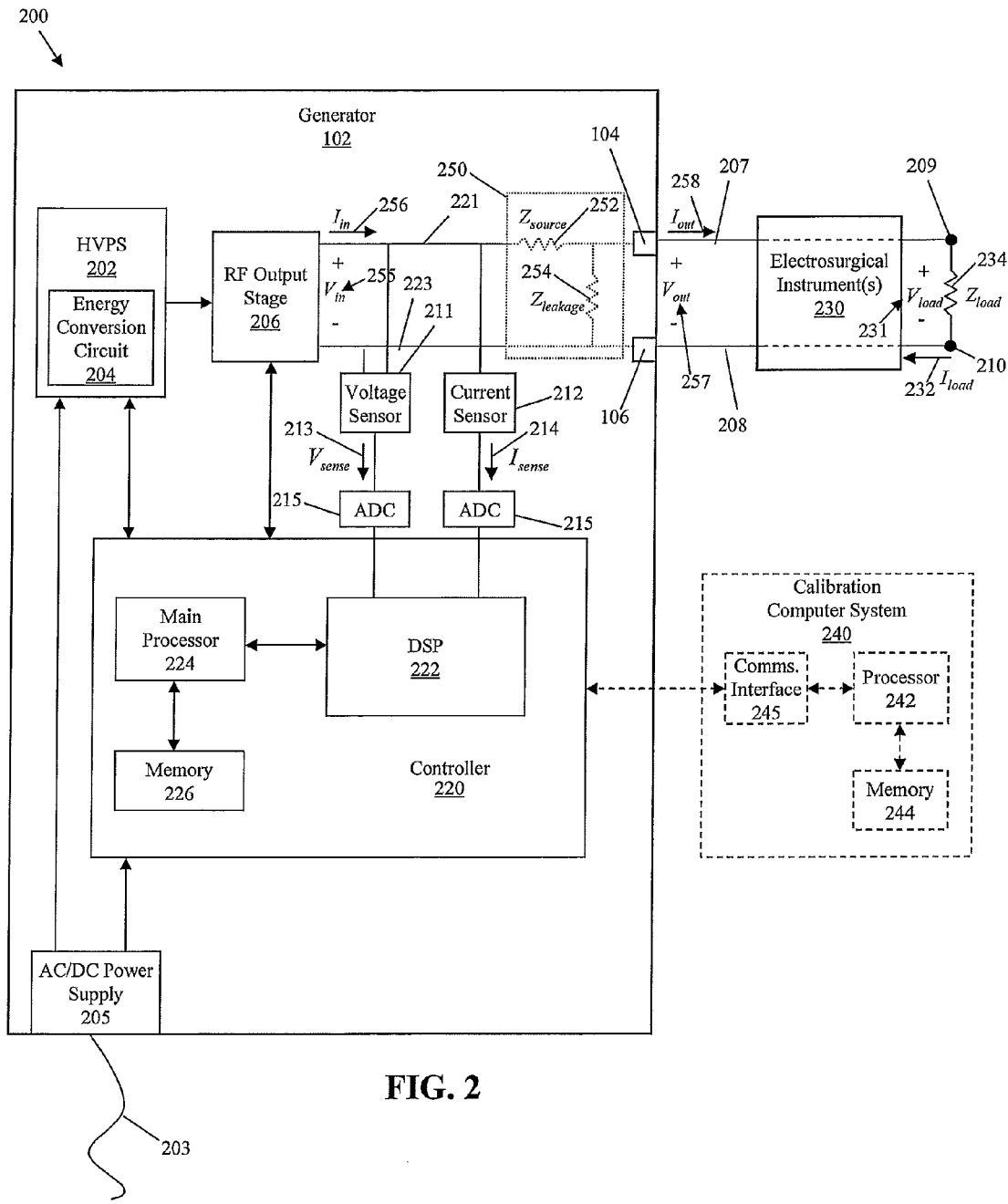
FIG. 2 is a block diagram of an electrosurgical system in communication with a calibration computer system according to embodiments of the present disclosure.

FIG. 2 is a block diagram of an electrosurgical system 200, which includes the generator 102 of FIG. 1 and a calibration computer system 240. The generator 102 of the electrosurgical system 100 includes a controller 220, a high voltage power supply 202, and a radio frequency output stage 206, which operate together to generate an electrosurgical signal to be applied to tissue through electrodes 209, 210 of an electrosurgical instrument 230. The controller 220 includes a digital signal processor (DSP) 222, a main processor 224, and a memory 226. The controller 220 may be any suitable microcontroller, microprocessor (e.g., Harvard or Von Neumann architectures), PLD, PLA, or other digital logic. Memory 226 may be volatile, non-volatile, solid state, magnetic, or other suitable storage memory.

The controller 220 may also include various circuitry that serve as an interface between the main processor 224 and other circuitry within the electrosurgical generator 102 (e.g., amplifiers and buffers). The controller 220 receives various feedback signals that are used by the main processor 224 and/or the DSP 222 to generate control signals to control various subsystems of the generator 102, including the HVPS 202 and the RF output stage 206. These subsystems are controlled to generate electrosurgical energy having desired characteristics for performing surgical procedures on tissue, which is represented in FIG. 2 by a load 234 ($Z_{load}$).

The generator 102 includes an AC/DC power supply 205 that receives power from an alternating current (AC) source 203. The AC/DC power supply converts the AC into direct current (DC) and provides the DC to the energy conversion circuit 204. The energy conversion circuit 204 then converts the DC power at a first energy level into DC power at a second, different energy level based upon control signals received from the controller 220. The energy conversion circuit 204 supplies the DC power at the second, different energy level to the RF output stage 206. The RF output stage 206 inverts the DC power to produce a high-frequency alternating current (e.g., RF AC), which is applied to tissue. For example, the RF output stage 206 may generate a high-frequency alternating current using push-pull transistors coupled to a primary side of a step-up transformer (not shown) contained within the RF output stage 206.

The electrosurgical generator 102 includes measurement circuitry that is configured to accurately determine voltage, current, impedance, and power at a tissue site so that the controller 220 can use this feedback information to accurately control the characteristics of the electrosurgical output. This measurement circuitry includes a voltage sensor 211 and a current sensor 212 coupled to the output of the RF output stage 206. The voltage sensor 211 senses the voltage across the output of the RF output stage 206 and provides an analog signal representing the sensed voltage 213 ($V_{sense}$) to an analog-to-digital converter (ADC) 215, which converts the analog signal into digital form. Similarly, the current sensor 212 senses the current at the output of the RF output stage 206 and provides an analog signal representing the sensed current 214 ($I_{sense}$) to another ADC 215, which converts the analog signal into digital form.

The DSP 222 receives the sensed voltage and sensed current data and uses it to calculate the impedance and/or the power at the tissue site. The main processor 224 of the controller 220 executes algorithms that use the sensed voltage, the sensed current, the impedance, and/or the power to control the HVPS 202 and/or the RF Output Stage 206. For example, the main processor 224 may execute a PID control algorithm based upon the calculated power and a desired power level, which may be selected by a user, to determine the amount of electrical current that should be supplied by the RF output stage 206 to achieve and maintain the desired power level at the tissue site.

To accurately control the electrosurgical energy applied to tissue, the controller 220 needs to accurately sense the voltage and current at the tissue. The voltage sensed by the voltage sensor 211 and the current sensed by the current sensor 212, however, may be inaccurate because of the RF impedance losses associated with the first and second transmission lines 221, 223 connected between the RF output stage 206 and the electrodes 209, 210. In other words, the voltage and current measured at the RF output stage 206 by the voltage and current sensors 211, 212 may not equal the actual voltage and current 231, 232 at the load (i.e., tissue) because of the RF impedance losses.

These RF impedance losses may be modeled as a source impedance 252 connected in series with the first transmission line 221 and a leakage impedance 254 connected between the first transmission line 221 and the second transmission line 223. This arrangement of the source impedance 252 and the leakage impedance 254 forms an impedance loss model 250. The voltage and current output from the RF output stage 206 (and sensed by the voltage and current sensors 211, 212, respectively) represent an input voltage 255 ($V_{in}$) and an input current 256 ($I_{in}$) respectively, applied to the impedance loss model 250. Also, the voltage and current output from the generator 102 and supplied to the load 234 ($Z_{load}$) represent an output voltage 257 ($V_{out}$) and an output current 258 ($I_{out}$), respectively, output from the impedance loss model 250.

To compensate for the impedance losses that introduce errors into the sensor data, the electrosurgical system 200 calibrates source and leakage impedance loss model parameters associated with the source impedance 252 and the leakage impedance 254 of the impedance loss model 250 and then calculates new sensed voltages and currents based upon these parameters. The new sensed voltages and currents represent accurate measurements of the voltage and current at the tissue.

The calibration process involves sensing a voltage and a current of an electrosurgical signal applied to a test load coupled to the output of the electrosurgical system, sensing a phase between the voltage and the current, and calculating a source impedance loss model parameter and a leakage impedance loss model parameter based upon the sensed voltage, the sensed current, the sensed phase, and a predetermined impedance of the test load. The predetermined impedance of the test load is measured with an impedance meter.

The impedance loss model parameters are calculated by an external calibration computer system 240 that is connectable to the controller 220 of the generator 102. The calibration computer system 240 includes a processor 242, a memory 244, and a communications interface 245. The processor 242 accesses measurement data, which includes sensor voltage values, sensor current values, and predicted phase values, via the communications interface 245 and stores the measurement data in the memory 244. Then, the processor 242 executes a calibration process to calculate the impedance loss model parameters based upon the measurement data. After executing the calibration process, the processor 242 loads the memory 226 of the controller 220 with the impedance loss model parameters. In some embodiments, the functions of the calibration computer system 240 are performed by the controller 220 of the generator 102.

During operation, the main processor 224 accesses the memory 226 to retrieve the calibrated impedance loss model parameters and provides them to the DSP 222. The DSP 222 uses the calibrated impedance loss model parameters and the voltage, current, and phase measurement data to calculate an accurate voltage, current, impedance, and/or power at the tissue site.

The accuracy of the calibration and compensation processes depends, in part, on the accuracy of the phase. The phase can be determined by sampling the sensed voltage and the sensed current and computing the phase between the sensed voltage and the sensed current. This method, however, requires complex algorithms and expensive, power-hungry, and high-speed hardware.

According to embodiments of the present disclosure, the internal transmission lines 221, 223 and the external cables 207, 208 of the electrosurgical system 200 are physically arranged and disposed so that the phase between the voltage and current applied to the tissue may be predicted using a simple equation and inexpensive, low-power, and low-speed hardware. In particular, the internal transmission lines 221, 223 and the external cables 207, 208 are configured so that they have a fixed and known reactance (i.e., the imaginary part of the impedance). For example, the turns of the internal transmission lines 221, 223 are specified so that they have a fixed and known reactance.

Thus, if external impedance changes (e.g., changes in tissue impedance) are dominated by changes in resistance as opposed to reactance, the phase between the sensed voltage and the sensed current can be predicted based upon sensed external impedance as shown in the following equation:

$$\varphi_{VI} = \arcsin\left(\frac{X}{|Z|}\right),$$

where X is the known reactance and |Z| is the absolute value of a sensed impedance. The absolute value of the sensed impedance is calculated by dividing a measured voltage by a measured current.

Figure 3:
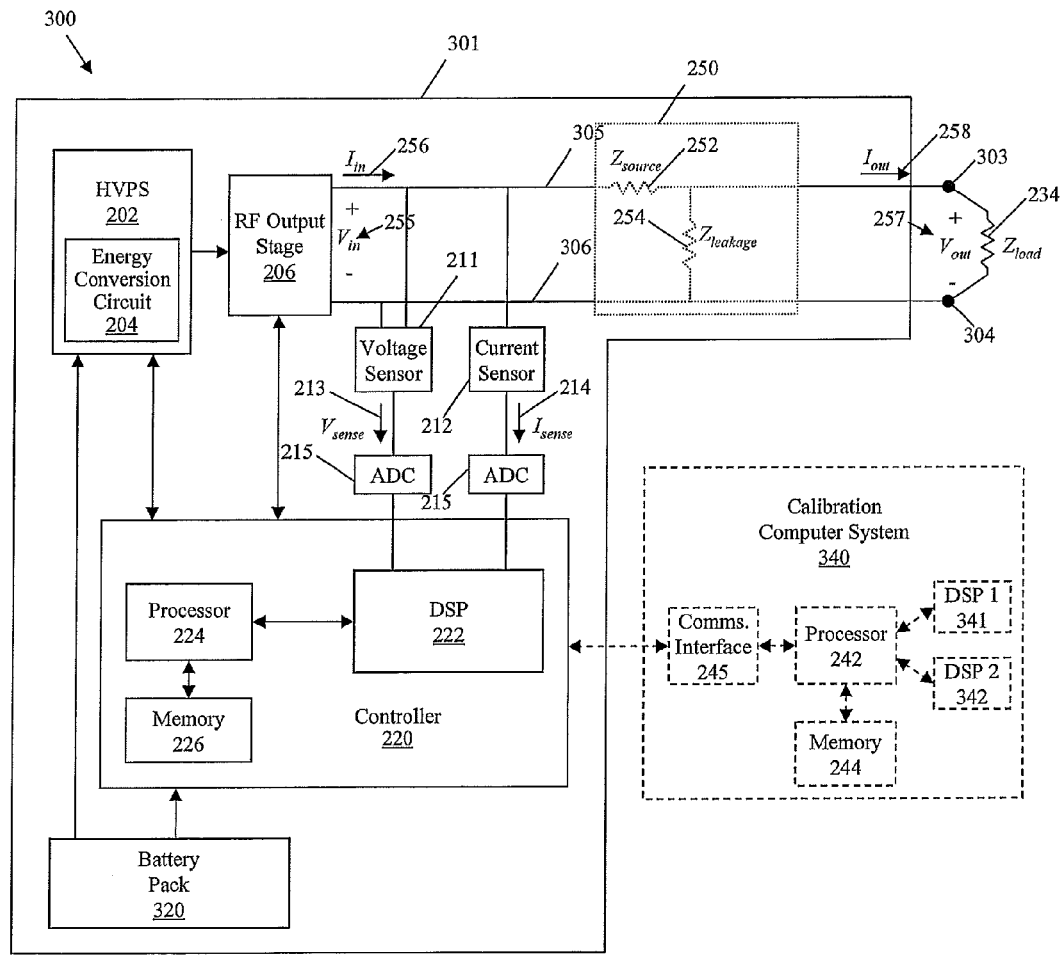
FIG. 3 is a block diagram of a portable handheld electrosurgical system in communication with a calibration computer system according to embodiments of the present disclosure.

FIG. 3 is a block diagram of an electrosurgical system 300 according to other embodiments of the present disclosure. The electrosurgical system 300 is similar to the electrosurgical system of FIG. 2, except that the generator 102 and the electrosurgical instrument 230 of FIG. 2 are both incorporated into a portable, handheld electrosurgical device 301. The handheld electrosurgical device 301 may incorporate a battery pack 320 that provides power to the various circuitry of the handheld electrosurgical device 301.

Like the electrosurgical system 200 of FIG. 2, the voltage sensed by the voltage sensor 211 and the current sensed by the current sensor 212 in the electrosurgical system 300 may not equal the actual voltage and current at the tissue site because of the RF impedance losses associated with the transmission lines 305, 306 that are connected between the RF Output Stage 206 and the electrodes 303, 304. The RF impedance losses may be modeled and compensated for by using the same impedance loss model 250 of FIG. 2.

As described above, the accuracy of the calibration and compensation processes depends, in part, on the accuracy of the phase. The phase can be determined by sampling the sensed voltage and the sensed current and computing the phase between the sensed voltage and the sensed current. This method, however, requires complex algorithms and expensive, power-hungry, high-speed hardware.

The internal transmission lines 305, 306 of the electrosurgical system 300 are physically arranged and disposed so that the phase between the voltage and current applied to the tissue may be predicted in a similar manner as described above with respect to the electrosurgical system 300 of FIG. 2. For example, the internal transmission lines 305, 306 are configured so that they have a fixed and known reactance (i.e., the imaginary part of the impedance). In particular, the turns of the internal transmission lines 305, 306 are specified so that they have a fixed and known reactance.

Figure 4:
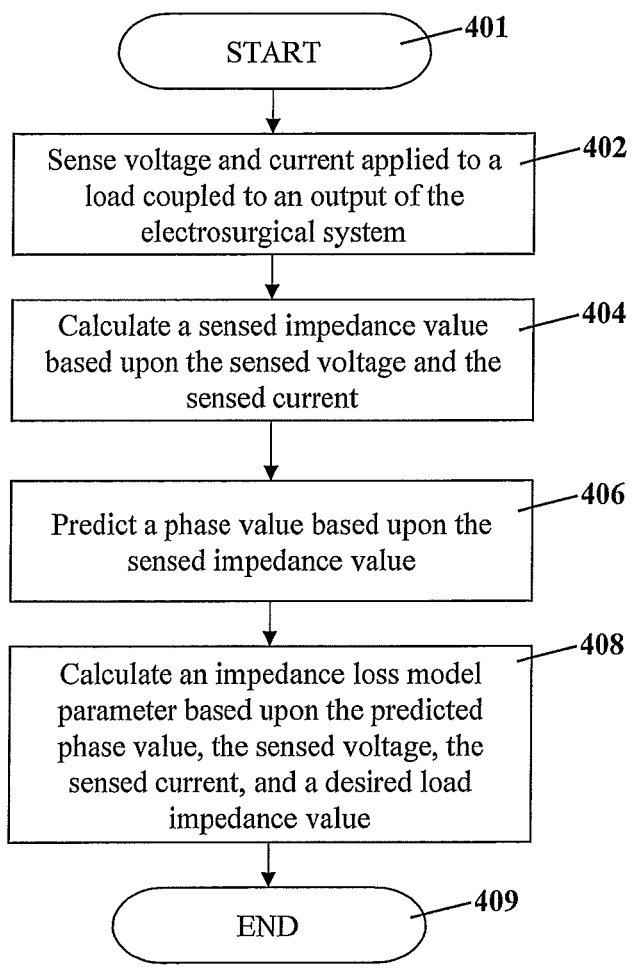
FIG. 4 is a flow diagram of a method of calibrating impedance loss model parameters according to some embodiments of the present disclosure.

FIG. 4 illustrates an impedance loss model calibration procedure according to embodiments of the present disclosure. Before the handheld electrosurgical device 301 is used to perform surgical procedures, a calibration procedure is performed to determine impedance loss model parameters (also referred to as cable compensation values). As shown in FIG. 4, the calibration procedure involves sensing a voltage and a current applied to a test load coupled to the electrodes of the electrosurgical device 301 (step 402), calculating a sensed impedance value based upon the sensed voltage and the sensed current (step 404), predicting the phase between the sensed voltage and the sensed current based upon the sensed impedance value (406), and calculating at least one impedance value (e.g., the value of the source impedance $Z_{source}$ 210 and/or the value of the leakage impedance $Z_{leakage}$ 210) based upon the predicted phase value, the sensed voltage, the sensed current, and a desired impedance of the test load (step 408).

For the calibration procedure, the test load may be a power resistor, a load resistor, or other resistive element that represents an impedance of tissue. In some embodiments, the desired impedance of the test load is the impedance measured using an impedance meter, e.g., an LCR meter, with the frequency set to the operational frequency of the electrosurgical device, e.g., 470 kHz.

Figure 5:
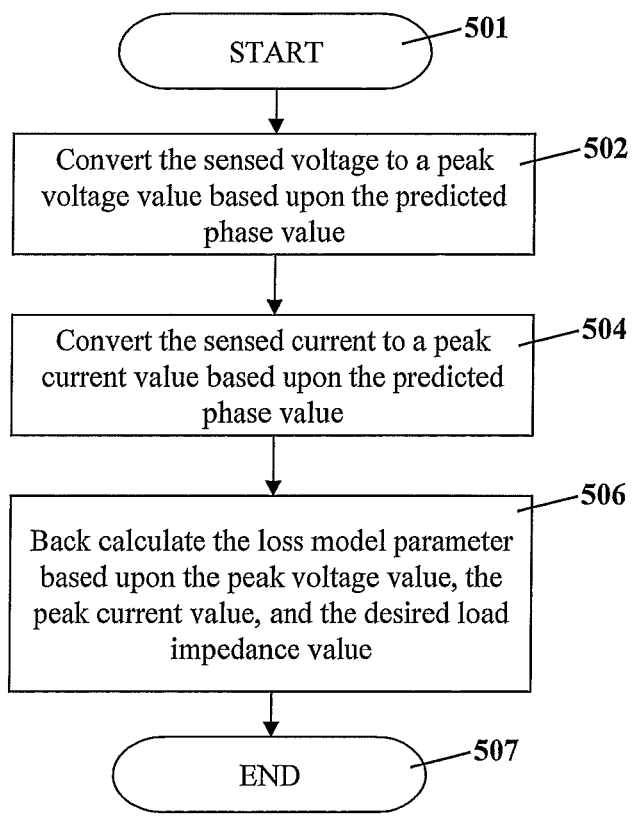
FIG. 5 is a flow diagram of the method of calculating the impedance loss model parameters of FIG. 4.
Figure 6:
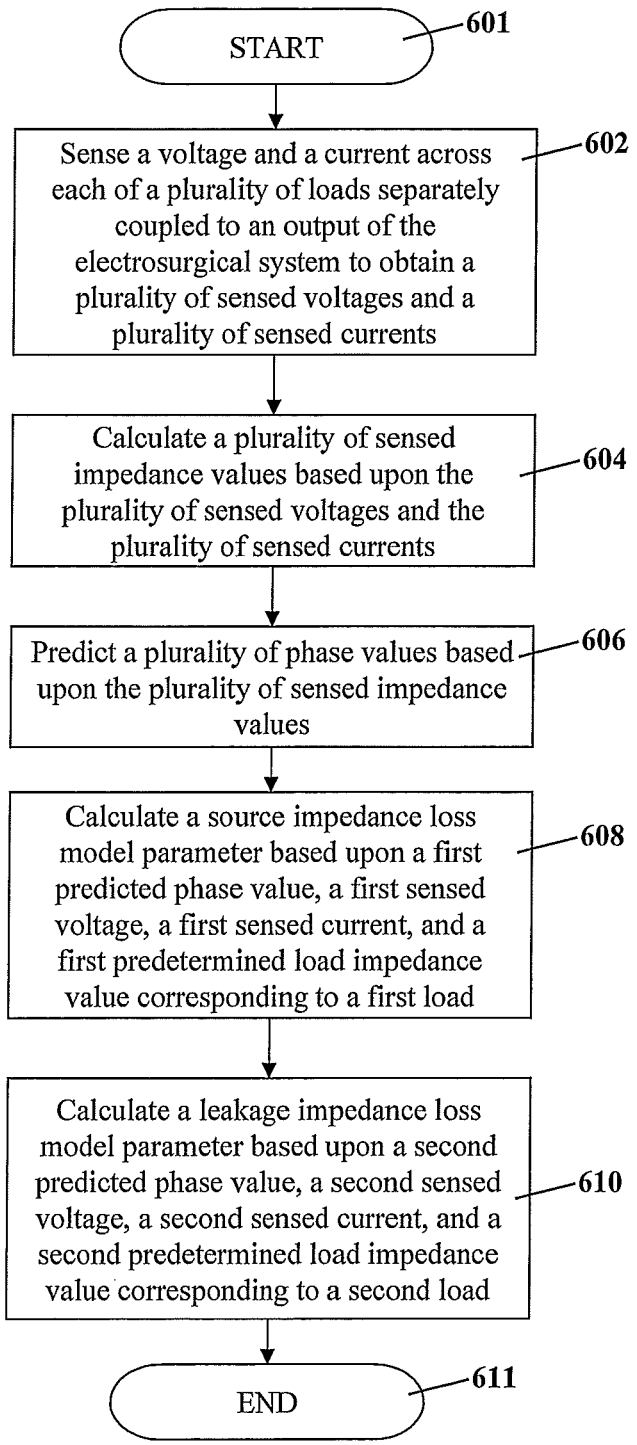
FIG. 6 is a flow diagram of a method of calibrating impedance loss model parameters, i.e., a source impedance parameter and a leakage impedance parameter, according to other embodiments of the present disclosure.

FIG. 5 is a flow diagram of the method of calculating the impedance loss model parameters of FIG. 4. First, the sensed voltage is converted to a peak voltage value based upon the predicted phase value (step 502). Similarly, the sensed current is converted to a peak current value based upon the predicted phase value (step 504). Then, the loss model parameter is back calculated based upon the peak voltage value, the peak current value, and the desired load impedance value FIG. 6 is a flow diagram of a method of calibrating impedance loss model parameters, i.e., a source impedance parameter and a leakage impedance parameter, according to other embodiments of the present disclosure. This calibration method uses multiple test loads having a range of rated resistance or impedance values because the reactance of the transmission lines or cables of the electrosurgical system varies based upon the impedance of the tissue. For example, source impedance losses are dominant for low resistance loads and leakage impedance losses are dominant for high resistance loads.

In some embodiments, the resistance of the power resistors may range between 0 ohms and 5000 ohms. In other embodiments, the resistance of the power resistors may range between 0 ohms and 1500 ohms.

First, a voltage and a current is sensed or measured across each of a plurality of test loads, e.g., power resistors, which are separately coupled to an output of the electrosurgical system to obtain a plurality of sensed voltages and a plurality of sensed currents (step 602). Voltage and current measurements are taken after an operating mode, e.g., bipolar standard, and an output port of the electrosurgical system, if any, are selected. Also, the control is set to closed-loop control and the output power is set to a desired level, e.g., 50 W for bipolar standard. In some embodiments, the rms voltage and rms current applied to each of the test loads ($V_{sense}$ and $I_{sense}$) are measured using the ADCs 215 disposed within the electrosurgical generators as shown in FIGS. 1 and 2.

Next, the sensed voltages and currents are used to calculate sensor impedance values for each of the test loads (step 604). For example, the sensor impedance values are calculated according to the following equation:

$$Z_{sense} = \frac{V_{sense}}{I_{sense}}.$$

These sensor impedance values are then used to predict the phase between the sensed voltage and sensed current for each of the test loads (step 606). For example, the predicted phase value may be calculated according to a polynomial function of the sensor impedance values. An example of such a polynomial function is:

$$\phi_{VI} = aZ_{load}^3 - bZ_{load}^2 + cZ_{load} - d,$$

where *the* polynomial coefficients *are:*

$a = 6.538 \times 10^{-12},$ $b = 1.0 \times 10^{-7},$ $c = 5.73 \times 10^{-4},$ and $d = 0.1766687.$ The polynomial function may be determined using known curve fitting techniques. The curve fitting techniques are used to approximate the change in phase based on absolute impedance measured over a varying external load ranging from a minimum load (e.g., 0 ohms) to a maximum load (e.g., 1500 or 5000 ohms) given a fixed internal source impedance and a fixed internal leakage impedance. In other words, as the real impedance (i.e., tissue resistance) changes from a minimum value to a maximum value and the imaginary impedance (i.e., reactance) remains fixed, there is a relationship between the absolute impedance and the real impedance. A curve fitting technique may be applied to fit a polynomial function to this relationship over the range of possible real impedance values (e.g., 0-1500 ohms).

The polynomial coefficients of the polynomial function determined by a curve fitting technique are unique for each particular generator. In some embodiments, the imaginary impedance (i.e., reactance) may be fixed across various manufacturing instances of a particular type of generator by specifying the number of turns of the RF transmission wires internal to the generator. In these embodiments, a common set of polynomial coefficients can be used for all generators of that particular type.

Before or during the calibration procedure, the test loads are separately connected to the leads of an impedance meter, e.g., an LCR meter, via test cables, e.g., short banana cables, to measure the impedance of each of the test loads. For example, the following power resistors having the following respective rated resistances may be measured to obtain the following respective measured impedance values:

| Power Resistor | Rated Resistance (ohms) | Measured Impedance (ohms) |
|---|---|---|
| Zload__05 | 5 | 5.0 + 2.0i |
| Zload__10 | 10 | 10.01 + 3.0i |
| Zload__20 | 20 | 20.01 + 5.07·i |
| Zload__50 | 50 | 50.08 + 1.62·i |
| Zload__100 | 100 | 100.43 + 6.40·i |
| Zload__200 | 200 | 201.05 + 7.54·i |
| Zload__300 | 300 | 301.35 + 9.74·i |
| Zload__500 | 500 | 502.24 + 3.84·i |
| Zload__1000 | 1000 | 1001.0 − 6.62·i |
| Zload__1500 | 1500 | 1501.0 − 12.0·i |

In some embodiments, the power resistors may further include a power resistor having a rated resistance of 0 ohms. If the impedance of the test cables, e.g., short banana cables, and the impedance of the test loads, e.g., power resistors, are measured together, then the impedances of the test cables is not included in the calibration calculations. If, on the other hand, the impedance of the test cables is measured separately from the impedance of the power resistors, then the impedance of the test cables are included in the calibration calculations. For example, the measured impedance of a first test cable (Cable 1) may be 0.0533+2.12i ohms and the measured impedance of a second test cable (Cable 2) may be 0.0305+1.62i ohms.

In some embodiments, the measured rms voltage, the measured rms current, the calculated phase, and the actual measured impedances of the test loads and test cable are formed into an input array, e.g.:

| $V_{sense(rms)}$ | $I_{sense(rms)}$ | $\phi_{VI}$ | $Z_{load(actual)}$ |
|---|---|---|---|
| 5.87354 | 1.79432 | −0.1749941 | Cable1 + Cable2 |
| 10.236 | 1.4174247 | −0.1725 | Zload__05 + Cable1 + Cable2 |
| 20.290839 | 1.5947771 | −0.1694 | Zload__10 + Cable1 + Cable2 |
| 49.453838 | 2.0342297 | −0.162798 | Zload__20 + Cable1 + Cable2 |
| 89.06355 | 1.681512 | −0.146599 | Zload__50 + Cable1 + Cable2 |
| 90.157114 | 0.901156 | −0.1203367 | Zload__100 + Cable1 + Cable2 |
| 89.970472 | 0.4828364 | −0.0733272 | Zload__200 + Cable1 + Cable2 |
| 89.78422 | 0.3280953 | −0.0272202 | Zload__300 + Cable1 + Cable2 |
| 90.344142 | 0.2036573 | 0.0584109 | Zload__500 + Cable1 + Cable2 |
| 89.784217 | 0.107226 | 0.2368501 | Zload__1000 + Cable1 + Cable2 |
| 89.970472 | 0.0747309 | 0.379646 | Zload__1500 + Cable1 + Cable2 |

This input array may be stored in the memory 244 of the calibration computer system 240 so that the processor 242 can retrieve the measurement data in the input array and calculate loss model parameters based upon the measurement data.

Referring again to FIG. 6, in step 608, a source impedance parameter is calculated based upon a first predicted phase value, a first sensed voltage, a first sensed current, and a first predetermined load impedance value corresponding to a first load. Then, in step 610, a leakage impedance parameter is calculated based upon a second predicted phase value, a second sensed voltage, a second sensed current, and a second predetermined load impedance value corresponding to a second load. The first and second predetermined load impedance values are obtained by measuring the impedances of the first and second loads, respectively, using an impedance meter. In some embodiments, the first and second predetermined load impedance values are selected from a plurality of predetermined load impedance values that are obtained by measuring the impedances of a plurality of loads using an impedance meter.

In some embodiments, the impedance loss model parameters are calculated using a back-calculation technique. According to the back-calculation technique, appropriate test load data is first selected to optimize measurement accuracy across a range of loads. For example, low impedance data, e.g., the data for the 5 ohm load, may be used to determine the source impedance loss model parameter and high impedance data, e.g., the data for the 1500 ohm load, may be used to determine the leakage impedance loss model parameter. Then, the impedance loss model parameters are calculated based upon measurement data (e.g., sensed voltage, sensed current, sensed phase, and predetermined impedance) for different test loads. For example, as described in more detail below, the source impedance loss model parameter is calculated based upon the measurement data for a low impedance load and the leakage impedance loss model parameter is calculated based upon the measurement data for a high impedance load.

Figure 7:
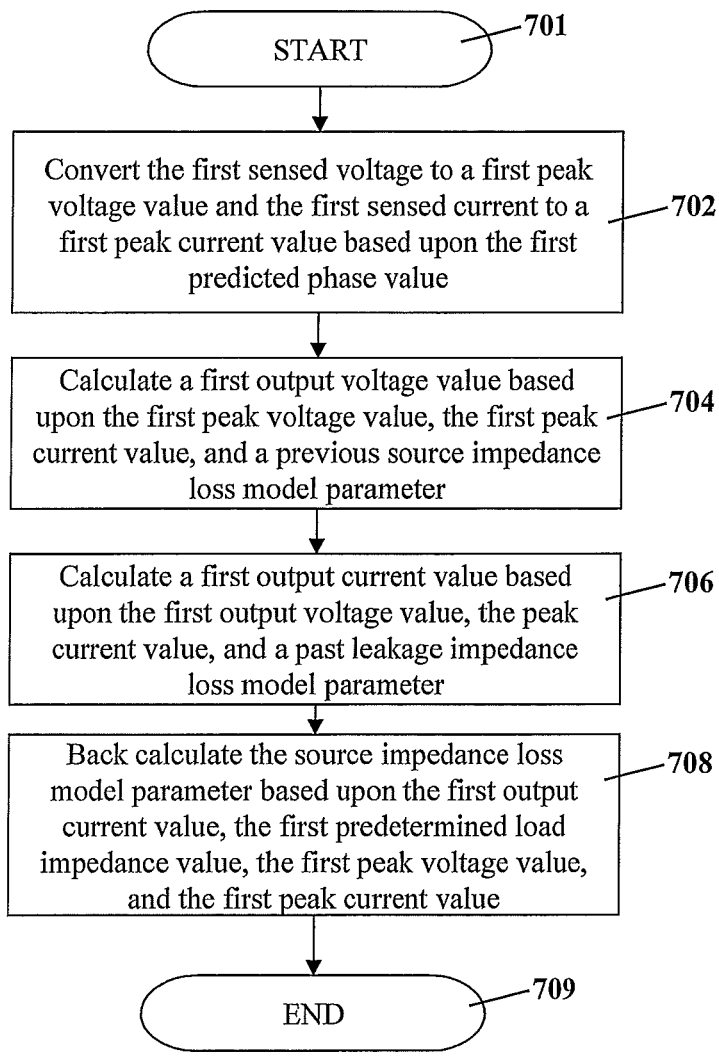
FIG. 7 is a flow diagram of a method of calculating the source impedance parameter of FIG. 6 according to some embodiments of the present disclosure.

FIG. 7 is a flow diagram of a method of calculating the source impedance loss model parameter of FIG. 6. In step 702, the first sensed voltage (e.g., a first voltage sensed by the voltage sensor 211 with a low impedance test load placed across the electrodes 303, 304) is converted to a first peak voltage value and the first sensed current (e.g., a first current sensed by the current sensor 212 with a low impedance test load placed across the electrodes 303, 304) is converted to a first peak current value based upon the first predicted phase value. For example, the first sensed voltage and first sensed current are converted to rectangular peak values according to the following equations:

$$I_{peak,1} = (I_{sense,1} \cdot \cos(\hat{\phi}_{VT,1}) + I_{sense,1} \cdot \sin(\hat{\phi}_{VT,1})) \cdot \sqrt{2}, \text{ and}$$

$$V_{peak,1} = V_{sense,1} \cdot \sqrt{2}$$

where $I_{peak,1}$ represents the first peak current value, represents the first sensed current, $\hat{\phi}_{VT,1}$ represents the first predicted phase value, $V_{peak,1}$ represents the first peak voltage value, and $V_{sense,1}$ represents the first sensed voltage.

Next, a first output voltage value is calculated based upon the first peak voltage value, the first peak current value, and a previous source impedance loss model parameter (also referred to herein as a previous source impedance parameter) (step 704). For example, the first output voltage value is calculated by first calculating a first source voltage ($V_{source,1}$), i.e., the voltage drop across the previous source impedance loss model parameter ($Z_{source}(n-1)$), according to the following equation:

$$V_{source,1} = I_{peak,1} \cdot Z_{source}(n-1).$$

In some embodiments, the previous source impedance parameter and the previous leakage impedance parameter are set to initial values before a first iteration of the loss model calibration procedure. Then, the first output voltage ($V_{out,1}$) is calculated according to the following equation:

$$V_{out,1} = V_{peak,1} - V_{source,1}$$

Next, a first output current value is calculated based upon the first output voltage value, the peak current value, and a previous leakage impedance loss model parameter (also referred to herein as a previous leakage impedance parameter) (step 706). For example, the first output current value ($I_{out,1}$) is calculated by first calculating a first leakage current, i.e., the current flowing through the previous leakage impedance loss model parameter ($Z_{leakage}(n-1)$), according to the following equation:

$$I_{leakage,1} = \frac{V_{out,1}}{Z_{leakage}(n-1)}.$$

In some embodiments, The first output current value is then calculated according to the following equation:

$$I_{out,1} = I_{peak,1} - I_{leakage,1}.$$

Finally, the source impedance loss model parameter is back calculated based upon the first output current value, the first predetermined load impedance value (e.g., a premeasured impedance value of a first test load), the first peak voltage value, and the first peak current value (step 708).

Figure 10:
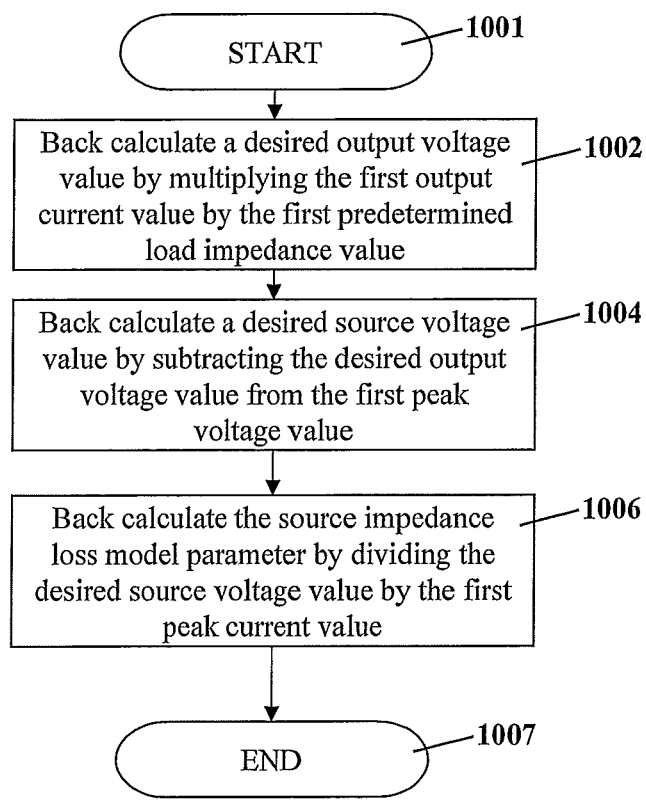
FIG. 10 is a flow diagram of a method of back calculating the source impedance parameter of FIGS. 7 and 9 according to some embodiments of the present disclosure.

A method of back calculating the source impedance loss model parameter is shown in FIG. 10. First, a desired output voltage value ($V_{out(desired)}$) is back calculated by multiplying the first output current value by the first predetermined load impedance value ($Z_{load,1}$), i.e.:

$$V_{out(desired)} = I_{out,1} \cdot Z_{load,1}.$$

Second, a desired source voltage $V_{source(desired)}$ is back calculated by subtracting the desired output voltage value from the first peak voltage value, i.e.:

$$V_{source(desired)} = V_{peak,1} - V_{out(desired)}.$$

Finally, the current source impedance loss model parameter $Z_{source}(n)$ is back calculated by dividing the desired source voltage value by the first peak current value, i.e.:

$$Z_{source}(n) = \frac{V_{source(desired)}}{I_{peak,1}}$$

Figure 8:
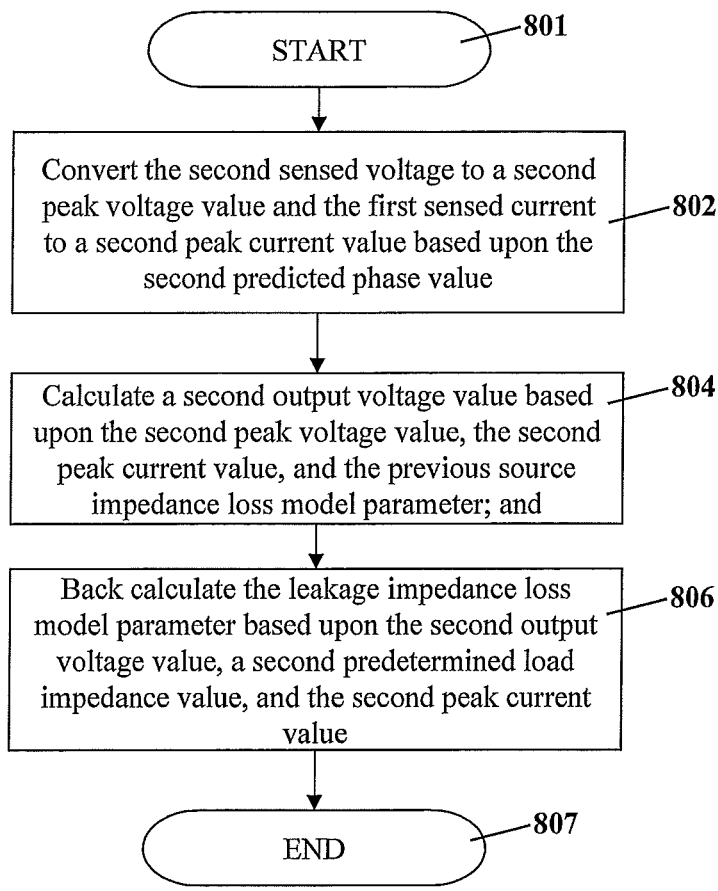
FIG. 8 is a flow diagram of a method of calculating the leakage impedance parameter of FIG. 6 according to some embodiments of the present disclosure.

FIG. 8 is a flow diagram of a method of calculating the leakage impedance loss model parameter of FIG. 6. In step 802, a second sensed voltage (e.g., a second voltage sensed by the voltage sensor 211 with a high impedance test load placed across the electrodes 303, 304) is converted to a second peak voltage value and a second sensed current (e.g., a second current sensed by the current sensor 212 with a high impedance test load placed across the electrodes 303, 304) is converted to a second peak current value based upon a second predicted phase value.

For example, the second sensed voltage and second sensed current are converted to rectangular peak values according to the following equations:

$$I_{peak,2} = (I_{sense,2} \cdot \cos(\hat{\phi}_{VT,2}) + I_{sense,2} \sin(\hat{\phi}_{VT,2})) \cdot \sqrt{2}, \text{ and}$$

$$V_{peak,2} = V_{sense,2} \cdot \sqrt{2},$$

where $I_{peak,2}$ represents the second peak current value $I_{sense,2}$ represents the second sensed current, $\hat{\phi}_{VT,2}$ represents the second predicted phase value, $V_{peak,2}$ represents the second peak voltage value, and $V_{sense,2}$ represents the second sensed voltage.

Next, a second output voltage value is calculated based upon the second peak voltage value, the second peak current value, and the previous source impedance loss model parameter (step 804). For example, the second output voltage value is calculated by first calculating a second source voltage ($V_{source,2}$), i.e., the voltage drop across the previous source impedance loss model parameter ($Z_{source}(n-1)$), according to the following equation:

$$V_{source,2} = I_{peak,2} \cdot Z_{source}(n-1),$$

Then, the second output voltage ($V_{out,2}$) is calculated according to the following equation:

$$V_{out,2} = V_{peak,2} - V_{source,2}$$

Finally, the leakage impedance loss model parameter is back calculated based upon the second output voltage value, the second predetermined load impedance value (e.g., a pre-measured impedance value of a second test load), and the second peak current value (step 708).

Figure 11:
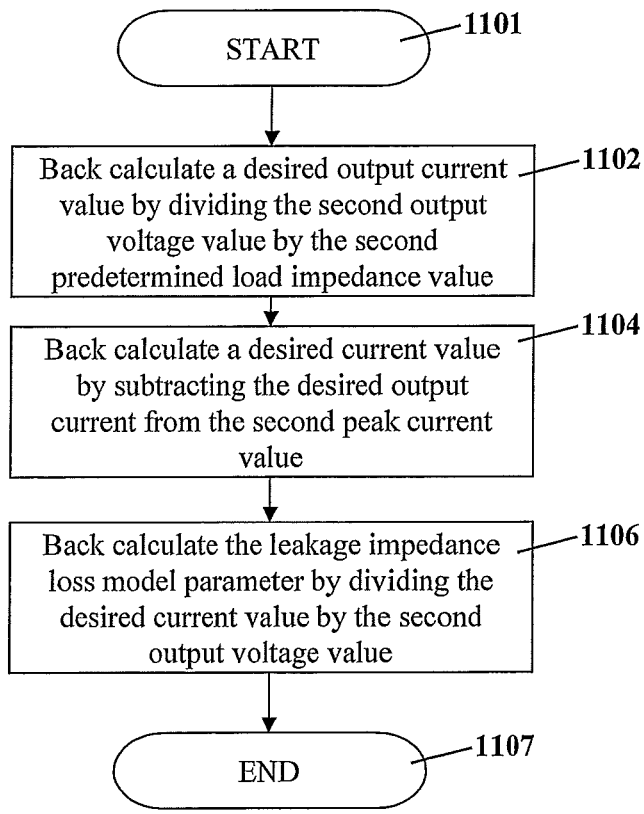
FIG. 11 is a flow diagram of a method of back calculating the leakage impedance parameter of FIGS. 8 and 9 according to some embodiments of the present disclosure.

A method of back calculating the leakage impedance loss model parameter is shown in FIG. 11. First, a desired output current value ($I_{out(desired)}$) is back calculated by dividing the second output voltage value by the second predetermined load impedance value ($Z_{load,2}$), i.e.:

$$I_{out(desired)} = \frac{V_{out,2}}{Z_{load,2}}.$$

Second, a desired leakage current $I_{leakage(desired)}$ is back calculated by subtracting the desired output current value from the second peak current value, i.e.:

$$I_{leakage(desired)} = I_{peak,2} - I_{out(desired)}.$$

Finally, the current leakage impedance loss model parameter $Z_{leakage}(n)$ is back calculated by dividing the second output voltage value by the desired leakage current value, i.e.:

$$Z_{leakage}(n) = \frac{V_{out,2}}{I_{leakage(desired)}}.$$

Figure 9:
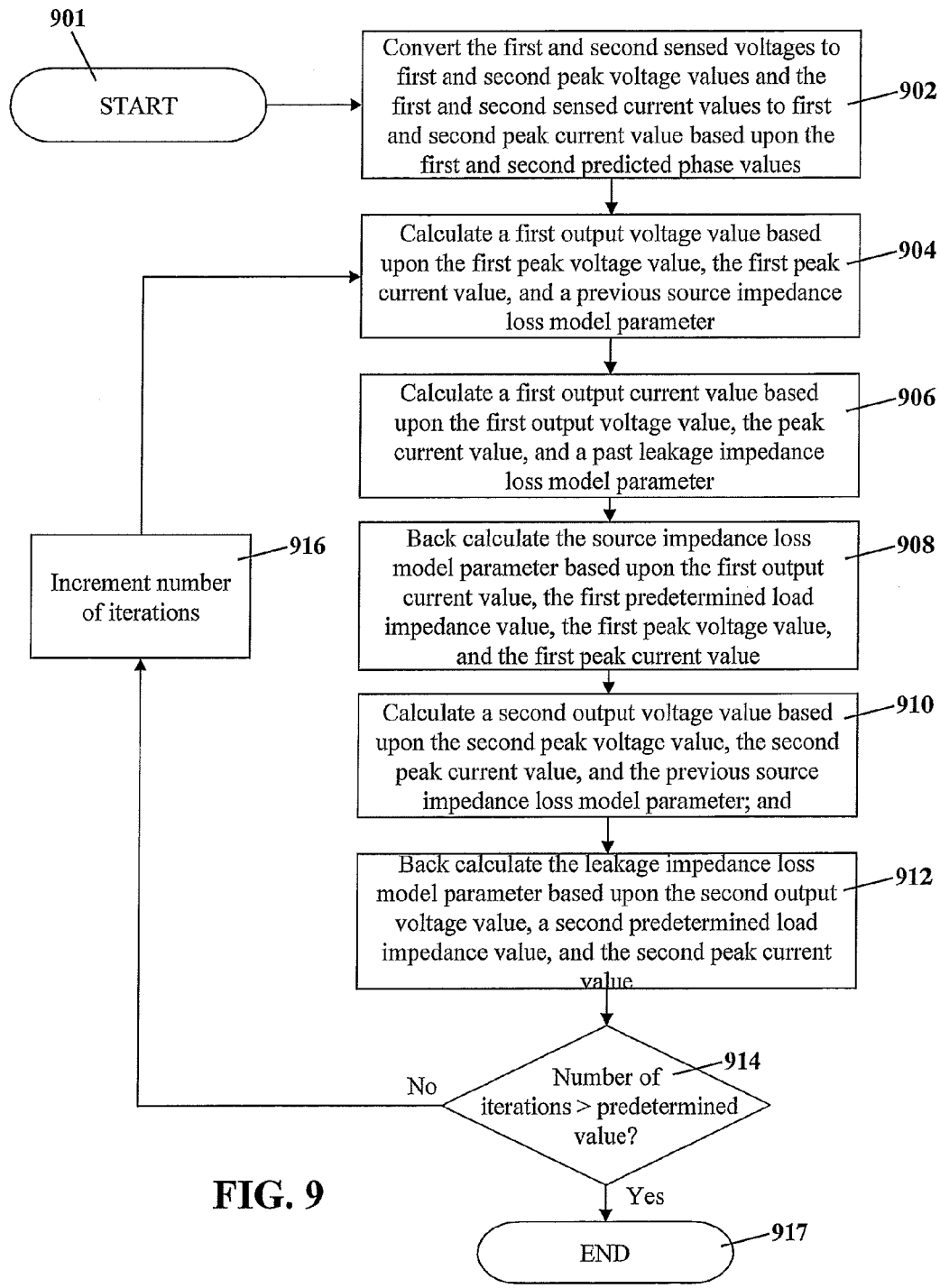
FIG. 9 is a flow diagram of a method of calculating the source impedance parameter and the leakage impedance parameter of FIG. 6 according to other embodiments of the present disclosure.

In some embodiments, the source impedance loss model parameter and the leakage impedance loss model parameter are calculated together in an iterative manner. An example method of iteratively calculating the impedance loss model parameters is shown in the flow diagram of FIG. 9. In step 902, first and second sensed voltages are converted to first and second peak voltage values and first and second sensed current values are converted to first and second peak current values based upon first and second predicted phase values. Next, in steps 904-908, which are identical to steps 704-708 of FIG. 7, the source impedance loss model parameter is calculated. Then, in steps 910-912, which are identical to steps 804-806 of FIG. 8, the leakage impedance loss model parameter is calculated.

Finally, in step 914, it is determined whether the number of iterations is greater than a predetermined value. If it is determined that the number of iterations is greater than the predetermined value, then the method of calculating the impedance loss model parameters ends in step 917. Otherwise, the number of iterations is incremented (e.g., by one) in step 916 and steps 904-912 are repeated. In some embodiments, the predetermined value is set to a number of iterations that produces accurate impedance loss model parameters.

In some embodiments, multiple redundant DSPs are used to determine the impedance loss model parameters to ensure accuracy. For example, as shown in FIG. 3, the calibration computer system 340 includes a first DSP 341 and a second DSP 342. The first DSP 341 calculates the source and leakage impedance loss model parameters according to the various methods described above and the second DSP 342 performs the same calculations. Then, the impedance loss model parameters calculated by the DSPs 341, 342 are averaged to obtain an average source impedance parameter and an average leakage impedance parameter. The processor 242 receives the average source impedance parameter and the average leakage impedance parameter and transmits them to the controller 220 via the communications interface 245. In other embodiments, the calibration computer system 340 is implemented in the controller 220 or the portable electrosurgical device 301 of FIG. 3.

Figure 12:
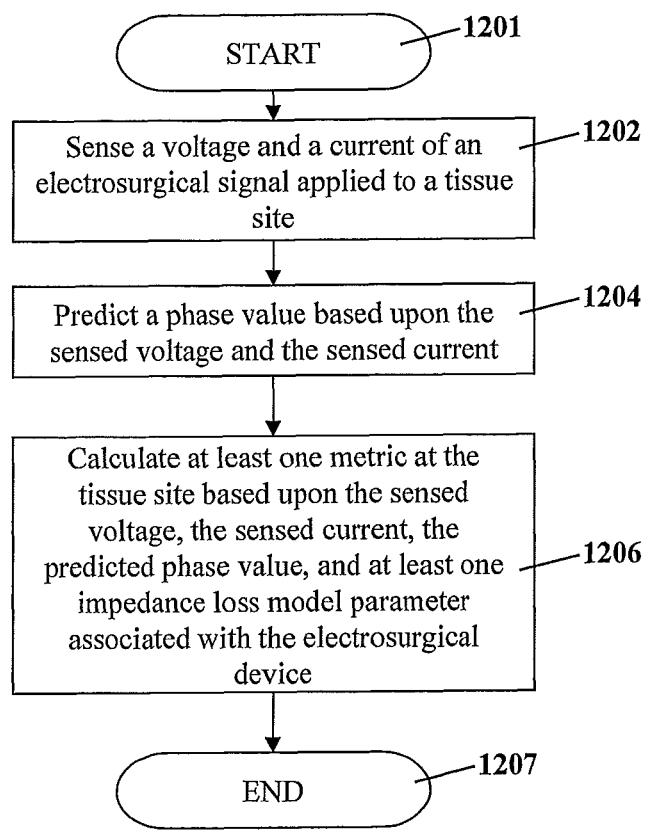
FIG. 12 is a flow diagram of a method of compensating for losses in an electrosurgical system according to embodiments of the present disclosure.

When the electrosurgical systems 200, 300 are used to perform surgical procedures, the calibrated impedance loss model parameters are used to compensate for the effect of impedance losses on the accuracy of the power and/or impedance measurements at the load. As shown in FIG. 12, the compensation process involves sensing a voltage and a current of an electrosurgical signal generated by and applied to a tissue site by the electrosurgical device (step 1202), predicting a phase value based upon the sensed voltage and the sensed current (step 1204), and calculating at least one metric at the tissue site based upon the sensed voltage, the sensed current, the predicted phase value, and at least one impedance loss model parameter associated with the electrosurgical system (step 1206). The at least one metric at the tissue site includes voltage, current, power, and/or impedance. Also, the at least one impedance loss model parameter includes a source impedance parameter and/or a leakage impedance parameter.

Figure 13:
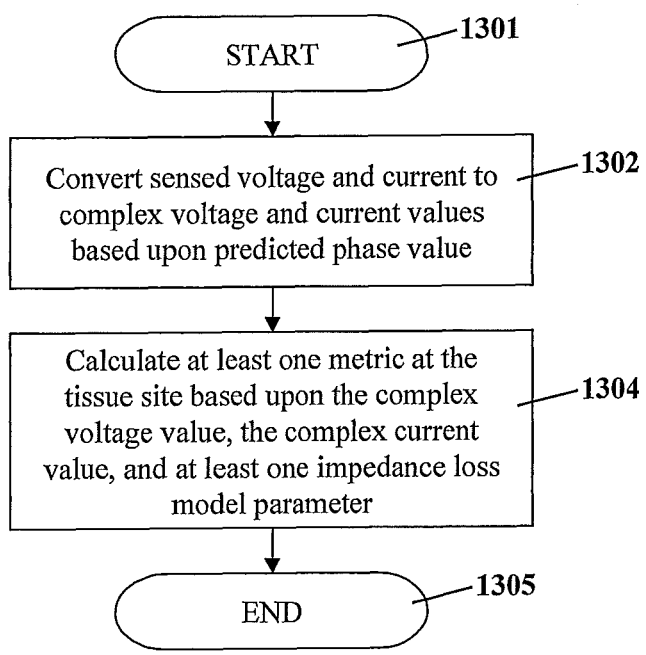
FIG. 13 is a flow diagram of a method of calculating at least one metric of FIG. 12 according to some embodiments of the present disclosure.

As shown in FIG. 13, calculating the at least one metric at the tissue site includes converting the sensed voltage to a complex voltage value based upon the predicted phase value (step 1302), converting the sensed current to a complex current value based upon the predicted phase value (step 1302); and calculating the at least one metric at the tissue site based upon the complex voltage value, the complex current value, and the at least one loss model parameter (step 1304).

Figure 14:
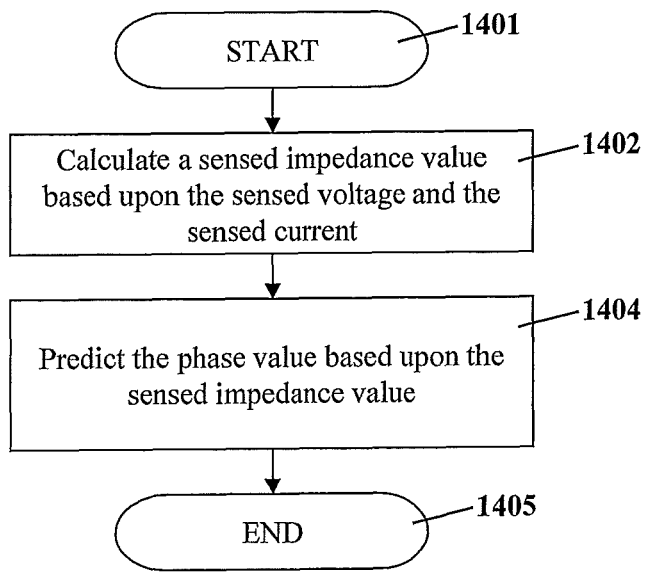
FIG. 14 is a flow diagram of a method of predicting the phase value of FIG. 12 according to some embodiments of the present disclosure.

As shown in FIG. 14, predicting the phase value includes calculating a sensed impedance value based upon the sensed voltage and the sensed current (1402) and predicting the phase value based upon the sensed impedance value (1404). In some embodiments, predicting the phase value is based upon a polynomial function of the sensed impedance value. The polynomial function may be a third-order polynomial function.

Figure 15:
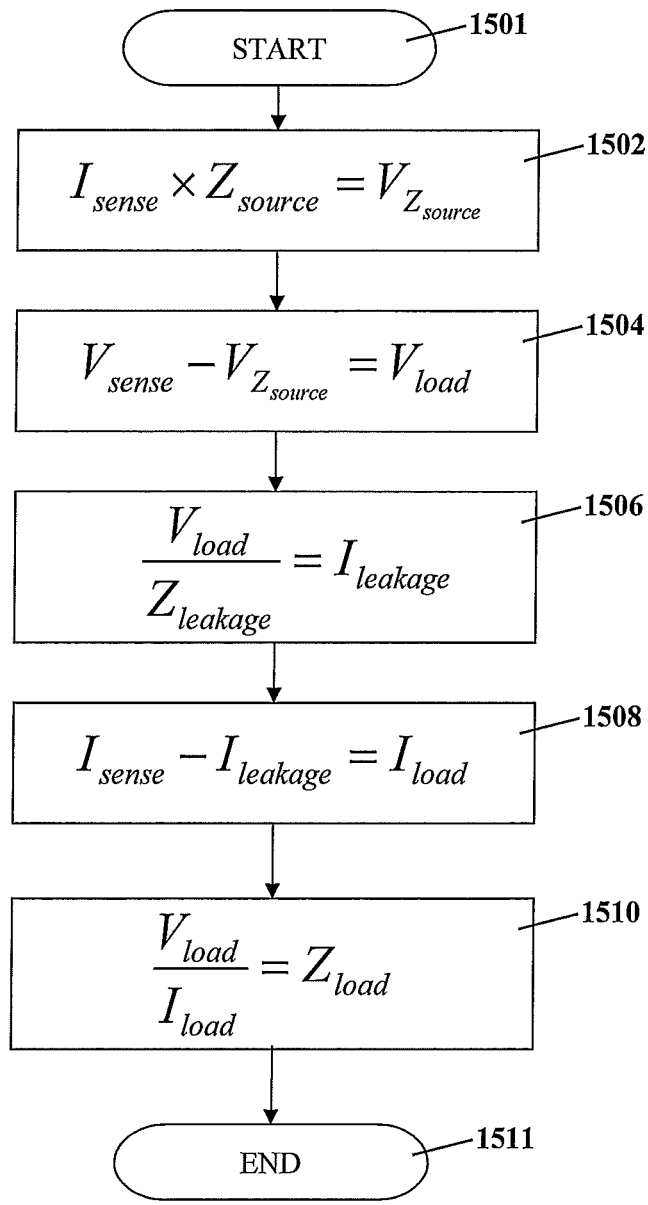
FIG. 15 is a flow diagram of a method of calculating at least one metric of FIG. 12 according to other embodiments of the present disclosure.

As shown in FIG. 15, calculating the at least one metric at the tissue site includes performing network solution calculations to determine the impedance at the tissue site. These calculations first involved multiplying the sensed current ($I_{sense}$) by the source impedance parameter ($Z_{source}$) to obtain a source impedance voltage value ($V_{Z_{source}}$) (step 1502). In step 1504, the source impedance voltage value ($V_{Z_{source}}$) is subtracted from the sensed voltage ($V_{sense}$) to obtain a load voltage value ($V_{load}$). In step 1506, the load voltage value ($V_{load}$) is divided by the leakage impedance parameter ($Z_{leakage}$) to obtain a leakage current value ($I_{leakage}$). In step 1508, the leakage current value ($I_{leakage}$) is subtracted from the sensed current ($I_{sense}$) to obtain a load current value ($I_{load}$). Finally, in step 1510, the load voltage value ($V_{load}$) is divided by the load current value ($I_{load}$) to obtain the load impedance value ($Z_{load}$). The load voltage value ($V_{load}$) and the load current value ($I_{load}$) can also be used to calculate the power at the tissue site.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method of determining impedance loss model parameters associated with a transmission line coupled between an electrosurgical generator and a load, comprising:
   sensing a voltage at an output of the electrosurgical generator;
   sensing a current at the output of the electrosurgical generator;
   calculating a sensed impedance value based upon the sensed voltage and the sensed current;
   predicting a phase value based upon the sensed impedance value to obtain a predicted phase value; and
   calculating the impedance loss model parameters, which include a parameter of a source impedance in series with the transmission line and a parameter of a leakage impedance in parallel with the load, based upon the predicted phase value, the sensed voltage, the sensed current, and a desired load impedance value.

2. The method of claim 1, wherein calculating the impedance loss model parameter includes:
   converting the sensed voltage to a peak voltage value based upon the predicted phase value;
   converting the sensed current to a peak current value based upon the predicted phase value; and
   calculating the impedance loss model parameter based upon the peak voltage value, the peak current value, the desired load impedance value, and a previous impedance loss model parameter.

3. A method of determining impedance loss model parameters associated with an electrosurgical device, comprising:
   sensing a voltage at an output of the electrosurgical device;
   sensing a current at the output of the electrosurgical device;
   calculating a plurality of sensed impedance values based upon the plurality of sensed voltages and the plurality of sensed currents;
   predicting a plurality of phase values based upon the plurality of sensed impedance values;
   calculating a source impedance parameter based upon a first predicted phase value of the plurality of phase values, a first sensed voltage of the plurality of sensed voltages, a first sensed current of the plurality of sensed currents, and a first predetermined load impedance value corresponding to a first load of the plurality of loads; and
   calculating a leakage impedance parameter based upon a second predicted phase value of the plurality of phase values, a second sensed voltage of the plurality of sensed voltages, a second sensed current of the plurality of sensed currents, and a second predetermined load impedance value corresponding to a second load of the plurality of loads.

4. The method of claim 3, wherein calculating the source impedance parameter includes:
   converting the first sensed voltage to a first peak voltage value based upon the predicted first phase value;
   converting the first sensed current to a first peak current value based upon the predicted first phase value;
   calculating a first output voltage value based upon the first peak voltage value, the first peak current value, and a previous source impedance parameter;
   calculating a first output current value based upon the first output voltage value, the peak current value, and a previous leakage impedance parameter; and
   calculating the source impedance parameter based upon the first output current value, the first predetermined load impedance value, the first peak voltage value, and the first peak current value.

5. The method of claim 4, wherein calculating the source impedance parameter includes:
   calculating a desired output voltage value by multiplying the first output current value by the first predetermined load impedance value;
   calculating a desired source voltage value by subtracting the desired output voltage value from the first peak voltage value; and
   calculating the source impedance parameter by dividing the desired source voltage value by the first peak current value.

6. The method of claim 4, wherein calculating the leakage impedance parameter includes:
   converting the second sensed voltage to a second peak voltage value based upon the predicted second phase value;
   converting the second sensed current to a second peak current value based upon the predicted second phase value;
   calculating a second output voltage value based upon the second peak voltage value, the second peak current value, and the previous source impedance parameter; and
   calculating the leakage impedance parameter based upon the second output voltage value, the second predetermined load impedance value, and the second peak current value.

7. The method of claim 6, wherein calculating the leakage impedance parameter includes:
   calculating a desired output current value by dividing the second output voltage value by the second predetermined load impedance value;
   calculating a desired current value by subtracting the desired output current from the second peak current value; and
   calculating the leakage impedance parameter by dividing the desired current value by the second output voltage value.

8. The method of claim 6, wherein calculating the leakage impedance parameter further includes iterating the steps of:
   calculating a first output voltage value;
   calculating a first output current value;
   calculating the source impedance parameter;
   calculating a second output voltage value; and
   calculating the leakage impedance parameter.

9. The method of claim 8, wherein the previous source impedance parameter and the previous leakage impedance parameter are set to initial values before a first iteration.

10. The method of claim 6, wherein the first predetermined load impedance value is less than the second predetermined load impedance value.

11. The method of claim 3, wherein predicting the plurality of phase values includes predicting the plurality of phase values based upon a polynomial function of the plurality of sensed impedance values.

12. The method of claim 11, wherein the polynomial function is a third-order polynomial function.

13. The method of claim 3, wherein the plurality of loads includes loads rated between 0 ohms and 5000 ohms.

14. The method of claim 3, further comprising sensing an impedance of each load of the plurality of loads using an impedance meter to obtain a plurality of predetermined load impedance values, the plurality of predetermined load impedance values comprising the first predetermined load impedance value and the second predetermined load impedance value.

15. A computer system for calibrating measurement circuitry of an electrosurgical device, comprising:
- a memory that stores measurement data including a plurality of voltage values sensed at an output of the electrosurgical device, a plurality of current values sensed at the output of the electrosurgical device, a plurality of predicted phase values, and a plurality of predetermined load impedance values;
- a processor coupled to the memory, the processor configured to (1) calculate a source impedance parameter based upon a first predicted phase value of the plurality of phase values, a first sensed voltage of the plurality of sensed voltage values, a first sensed current of the plurality of sensed current values, and a first predetermined load impedance value, and (2) calculate a leakage impedance parameter based upon a second predicted phase value of the plurality of phase values, a second sensed voltage of the plurality of sensed voltage values, a second sensed current of the plurality of sensed current values, and a second predetermined load impedance value; and
- a communications interface that transmits the source impedance parameter and the leakage impedance parameter to the measurement circuitry of the electrosurgical device.

16. The computer system of claim 15, wherein the communications interface receives the plurality of sensed voltage values and the plurality of sensed current values from the electrosurgical device and stores the plurality of sensed voltage values and the plurality of sensed current values in the memory.

17. The computer system of claim 15, wherein the processor is a first processor, the source impedance parameter is a first source impedance parameter, and the leakage impedance parameter is a first leakage impedance parameter, and
wherein the computer system further comprises a second processor that:
- calculates a second source impedance parameter based upon the first predicted phase value of the plurality of phase values, the first sensed voltage of the plurality of sensed voltage values, the first sensed current of the plurality of sensed current values, and the first predetermined load impedance value;
- calculates a second leakage impedance parameter based upon the second predicted phase value of the plurality of phase values, the second sensed voltage of the plurality of sensed voltage values, the second sensed current of the plurality of sensed current values, and the second predetermined load impedance value;
- averages the first source impedance parameter and the second source impedance parameter to obtain an average source impedance parameter; and
- averages the first leakage impedance parameter and the second leakage impedance parameter to obtain an average leakage impedance parameter, wherein the communications interface transmits the average source impedance parameter and the average leakage impedance parameter to the measurement circuitry of the electrosurgical device.

\* \* \* \* \*